United States Patent [19]

Klopotek

[11] Patent Number: 5,360,424
[45] Date of Patent: Nov. 1, 1994

[54] TRACKING SYSTEM FOR LASER SURGERY

[75] Inventor: Peter J. Klopotek, Framingham, Mass.

[73] Assignee: Summit Technology, Inc., Waltham, Mass.

[21] Appl. No.: 72,528

[22] Filed: Jun. 4, 1993

[51] Int. Cl.$^5$ .............................................. A61N 5/06
[52] U.S. Cl. ......................................... 606/4; 606/5; 606/17
[58] Field of Search ...................... 606/4–6, 606/10–13, 17–19

[56] References Cited

U.S. PATENT DOCUMENTS

| | | |
|---|---|---|
| 3,262,122 | 7/1966 | Fleisher et al. . |
| 3,558,208 | 1/1971 | Hudson . |
| 3,665,483 | 5/1972 | Becker et al. . |
| 4,139,409 | 2/1979 | Macken et al. . |
| 4,388,517 | 6/1983 | Schulte et al. . |
| 4,414,059 | 11/1983 | Blum et al. . |
| 4,443,075 | 4/1984 | Crane . |
| 4,461,294 | 7/1984 | Baron . |
| 4,648,400 | 3/1987 | Schneider et al. . |
| 4,686,979 | 8/1987 | Gruen et al. . |
| 4,732,148 | 3/1988 | L'Esperance, Jr. . |
| 4,856,513 | 8/1989 | Muller . |
| 4,973,330 | 11/1990 | Azema et al. .......................... 606/5 |
| 4,994,058 | 2/1991 | Raven et al. . |
| 5,019,074 | 5/1991 | Muller . |
| 5,147,352 | 9/1992 | Azema et al. . |
| 5,226,903 | 7/1993 | Mizuno ................................ 606/10 |

FOREIGN PATENT DOCUMENTS

| | | |
|---|---|---|
| 0412789A1 | 2/1991 | European Pat. Off. . |
| 9011054 | 10/1990 | WIPO ................................. 606/6 |
| WO92/15034 | 9/1992 | WIPO . |

OTHER PUBLICATIONS

J. P. Coullahan et al., "Chip Passivation Technique", IBM Technical Disclosure Bulletin, vol. 22, No. 6, Nov. 1979, pp. 2279, 2280, 2281, 285, 2531.
Puliafito et al., "Excimer Laser Ablation of the Cornea and Lens, Experimental Studies", Ophthalmology, vol. 92, No. 6, Jun. 1985, pp. 741–748.
Stephen L. Trokel M.D. et al., "Excimer Laser Surgery of the Cornea", American Journal of Ophthalmology, 1983, 96:710–71.
D. J. O'Hara et al., "Holographic Selective Heating System", IBM Technical Disclosure Bulletin, vol. 11, No. 9, Feb. 1969, pp. 1168–1169.
European Search Report issued on Feb. 9, 1994 in connection with related foreign application filed on May 3, 1993, International Application No. PCT/US/93/04171.
R. Juday, "Compensating for Movement of Eye in Laser Surgery", NTIS Tech Notes, p. 214, Mar. 1992.

Primary Examiner—Stephen C. Pellegrino
Assistant Examiner—Michael Peffley
Attorney, Agent, or Firm—Thomas J. Engellenner

[57] ABSTRACT

Systems and methods are disclosed for aligning and confining laser beam exposure to a defined target region of biological tissue during laser surgery by employing a floating lens which is mechanically coupled to a reference element, such as a target tissue securing assembly, in order to compensate for movements of the target during surgical procedures. The floating lens forms part of the imaging optics and, by its design, direct the laser beam to follow the movements of the target tissue regardless of translational movements of the target.

11 Claims, 6 Drawing Sheets

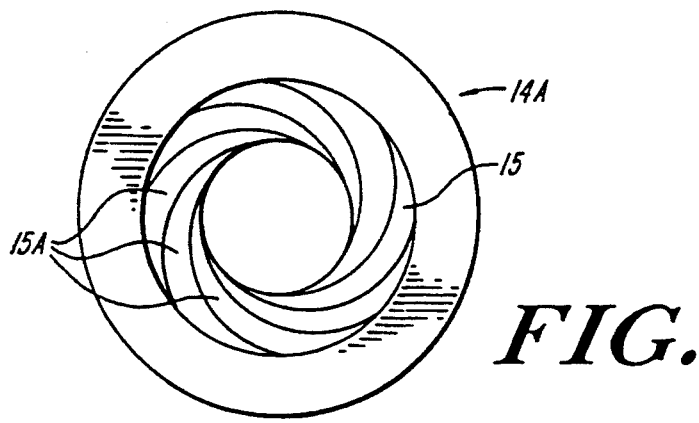
FIG. 2
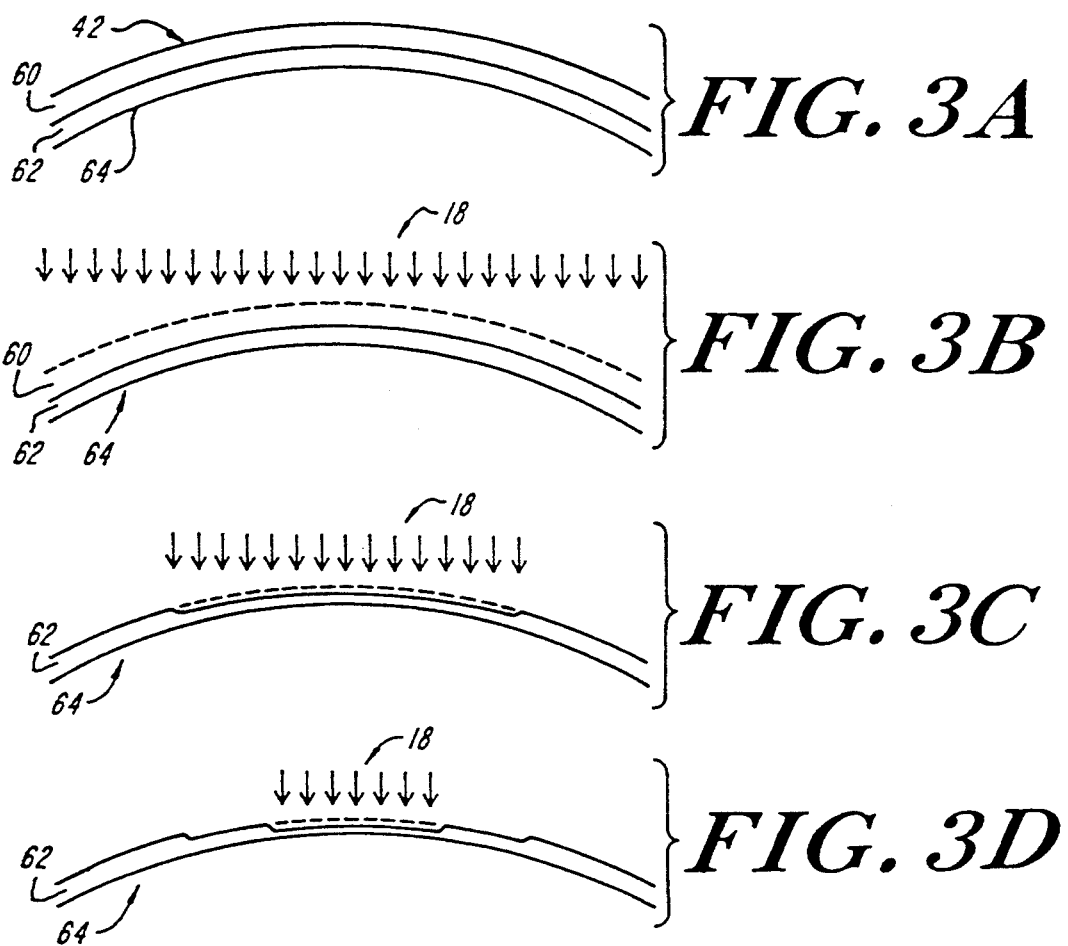
FIG. 3A
FIG. 3B
FIG. 3C
FIG. 3D

TRACKING SYSTEM FOR LASER SURGERY

BACKGROUND OF THE INVENTION

The technical field of this invention is laser surgery in which a laser is used to ablate biological tissue or otherwise treat regions of the body by irradiation and, in particular, is directed to systems and methods for precisely aligning and confining laser beam exposure to a defined target region during such surgery.

It is known to employ laser sources to erode, ablate, coagulate, alter or otherwise treat surfaces of biological materials. Such laser apparatus is in general relatively complex and demands highly skilled use. For example, laser ablative techniques have been proposed to modify the shape of sensitive surfaces, such as the cornea of the eye to correct vision defects. Extreme care must be taken to confine the ablative procedures to the upper layers of the cornea and to avoid damage to the basement membrane and the posterior endothelial lining of the cornea in such operations.

The use of a laser beam as a surgical tool for cutting incisions, a so-called laser scalpel, has been known for some time (see, for example, U.S. Pat. No. 3,769,963 issued to Goldman et al.). Lasers have also been employed for removal of skin pigmentation abnormalities, "birthmarks," scars, tattoos and the like. Furthermore, lasers have been used for photocoagulation of blood vessels, fusion of biological tissue and selective ablation of delicate biological structures, including the reprofiling or reshaping of the cornea of the eye to correct refractive errors in vision.

A technique for corneal reshaping, involving the use of a laser photoablation apparatus, is known in which the size of the area on the surface to which the pulses of laser energy are applied is varied to control the reprofiling operation. In one preferred embodiment, a beam-shaping shaping stop or window is moved axially along the beam to increase or decrease the region of cornea on which the laser radiation is incident. By progressively varying the size of the exposed region, a desired photoablation profile is established in the surface. For further details on this technique, see also Marshall et al., "Photo-ablative Reprofiling of the Cornea Using an Excimer Laser: Photorefractive Keratectomy," Vol. 1, *Lasers in Ophthalmology*, pp. 21–48 (1986), and U.S. Pat. No. 4,941,093 issued to Marshall et al., both of which are herein incorporated by reference.

Another approach involves the use of a graded intensity or photodecomposable mask which varies the laser transmission to the target surface, thereby inducing variable ablative depths on the surface. For example, U.S. Pat. No. 4,856,513 entitled "Laser Reprofiling Systems And Methods" which describes methodology for selectively eroding the cornea through the use of an erodable mask. The mask absorbs the surface laser radiation in varying amounts across the corneal surface to provide the desired surface profiles.

One problem of particular noteworthiness in laser corneal surgery and the like is the need for precise alignment of the laser and the target region. Even slight movements of the target can create problems insofar as the reprofiling operations are typically dependent upon the cumulative effects of a number of precisely aligned, discrete ablation steps. Moreover, in some procedures, the problem resides not only in precise positioning of the laser with respect to the eye or other target, but also in precise positioning of intermediate optical components, such as, for example, alignment and angular orientation of a beam-shaping mask or aperture. While gross eye movements can be prevented through the use of a eye restraining cup or the like, the problem of minor movements remains.

Various techniques have been described for tracking eye movements. However, these techniques are usually based on computer tracking or modeling of the eye, coupled with pattern recognition algorithms which attempt to detect, and/or compensate for, eye movements in real time. Such approaches have proved difficult to implement. Even when the eye movements can be monitored in real time, the hardware necessary to steer a laser beam in synchrony with such movements is, likewise, technologically complex and proned to errors. There exist a need for better techniques for tracking eye movements and for precisely aligning and confining laser beam exposure to the target region of the eye during laser surgery.

It is, therefore, an object of the present invention to address the problem of eye tracking, such that compensation can be provided for slight involuntary or inadvertent motions during ophthalmic surgery. More generally, it is an object of the invention to provide better and more reliable tracking mechanisms for laser surgical systems of various types whenever precise alignment with a target is necessary or desirable.

SUMMARY OF THE INVENTION

Systems and methods are disclosed for aligning and confining laser beam exposure to a defined target region of biological tissue during laser surgery by employing a floating lens which is mechanically coupled to the target, in order to compensate for movements of the target during surgical procedures. The floating lens forms part of the imaging optics, and by its design, directs the laser beam to follow the movements of the target tissue.

In one embodiment, a system is disclosed for tracking eye movements during laser ophthalmic surgery including an eye securing element (such as an eye cup) for securing an eye during surgery and an optical subsystem for projecting ablative radiation onto a defined target region of the eye. The optical subsystem further includes at least one fixed optical element which is fixed in position during surgery, and at least one floating optical element which is mechanical coupled to the eye securing element for movement therewith. The fixed optical element and the floating element form an imaging system in which movements of eve are tracked by the floating optical element, such that the ablative radiation remains imaged upon the target region.

The laser beam delivery system can employ two subsystems. The first subsystem can have at least one optically-active component, such as a lens or mirror, which is located in a fixed position in reference to the laser beam (e.g., in reference to the main body of the entire laser surgical system). The second subsystem can be a floating one having several degrees of freedom in reference to laser beam or the main body of the laser surgical system. The two subsystems form an imaging system, imaging an object located in the object plane, (e.g., an iris, mask, or stop) onto an image plane in such a manner that the changes in the position of the image spot follow or track any changes in the position of the floating subsystem along its degrees of freedom. The floating subsystem has, in one preferred embodiment, a target reference member, such as an eye cup and handle for manual operation, rigidly attached to its floating structure.

The spatial position of the reference member can be controlled directly by the clinician or the reference member and can be attached directly to the tissue. The first approach allows the clinician to direct freely the laser beam to a selected tissue location. The second approach constrains the laser beam instead to follow the movements of the attached tissue.

The invention will next be described in connection with certain illustrated embodiments; however, it should be clear that various changes, additions and subtractions can be made without departing from the spirit or scope of the invention. In particular, it should be appreciated that the mechanical linkages illustrated in the following drawings are only one of a number of ways that comply can be achieved between a target securing member and a floating lens. The linkages can be linear, proportional or non-linear depending upon the application.

BRIEF DESCRIPTION OF THE DRAWINGS

A more complete understanding of the invention may be obtained by reference to the drawings in which:

FIG. 2 illustrates a light restricting element incorporating an adjustable iris for use in the system of FIG. 1;

FIG. 3A through 3D illustrate diagrammatically successive steps in reprofiling a cornea with the adjustable iris of FIG. 2 to correct myopia;

DETAILED DESCRIPTION

Figure 1:
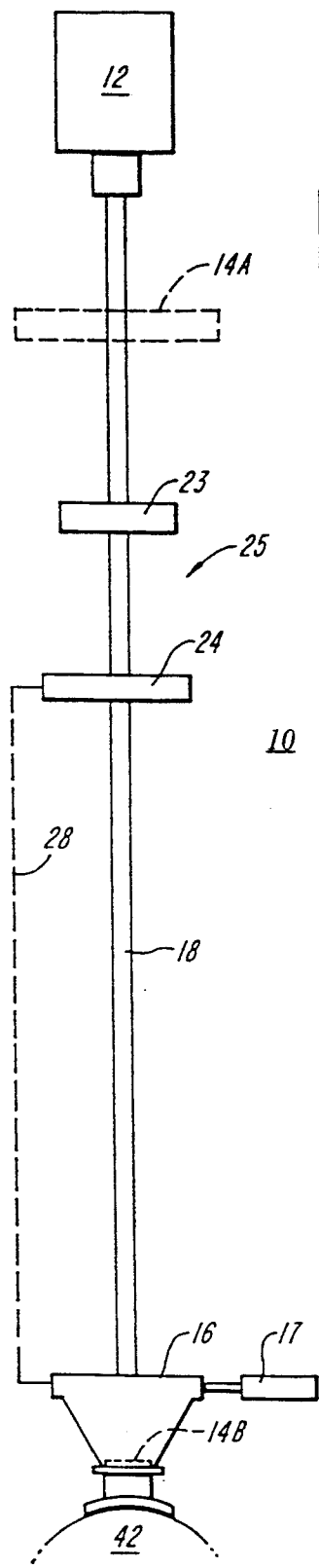
FIG. 1 is a diagrammatic illustration of a tracking system for laser ophthalmic surgery in accordance with the invention.

FIG. 1 illustrates system 10 for aligning and confining a laser beam 18 to a defined target region 42, such as an eye during laser surgery. The system 10 can include a laser source 12 for delivering ablative laser radiation, a light restricting element 14A and/or 14B for varying the exposure area over time, and an eye cup or other target reference member 16 for coupling the target to a tracking system 20. (It should be appreciated that the light restricting element 14A/14B may not be needed in all embodiments; for example, if the laser beam 18, itself, has a suitable intensity profile, a selective reprofiling procedure can be carried out without modifying the beam shape or size over time.) Optionally, the system can further include a handle 17 for manually directing the laser beam 18 to a desired target region.

In accordance with the present invention, the tracking system includes an optical subsystem 25 for projecting the ablative radiation onto the defined target region 42, including at least one fixed optical element 22 and at least floating optical element 24 which is mechanically coupled to the eye cup 16 or other target reference member via linkage 28. The fixed optical element 22 and the floating element 24 will both typically be lens elements and will together form an imaging system in which movements of the target are tracked by the floating element 24 so that the ablative radiation remains imaged upon the target region despite minor translational motion.

In FIG. 1, laser 12 can be a pulsed laser source, and the target surface 42 can be a cornea, optically aligned to the laser 12. The laser, for example, can be an excimer laser, and one preferred laser is an Argon-Fluoride laser having an ultraviolet (UV) characteristic emission wavelength of about 193 nanometers. Alternatively, other pulsed UV lasers having both shorter wavelengths down to about 157 nanometers (e.g., a Fluoride laser) and longer wavelengths up to about 300 nanometers may be useful in particular applications. In other embodiments, mid infrared (IR) laser sources such as Erbium:YAG lasers (emitting at about 2,940 nanometers) generating pulsed radiation at wavelengths strongly absorbed by water can also be employed to produce ablative effects.

Suitable irradiation intensities vary depending on the wavelength of the laser, and the nature of the irradiated object. For any given wavelength of laser energy applied to any given material, there will typically be a threshold value of energy density below which significant erosion does not occur. Above the threshold density, there will be a range of energy densities over which increasing energy densities give increasing depths of erosion until a saturation value is reached. For increases in energy density above the saturation value, no significant increase in erosion occurs.

The threshold value and the saturation value vary from wavelength to wavelength of laser energy and from material to material of the surface to be eroded, in a manner which is not easily predictable. However, for any particular laser and any particular material, the values can be found readily by experiment.

For example, in the case of ablating either Bowman's membrane or the stromal portion of the cornea by energy of wavelength 193 nanometers (the wavelength obtained from an ArF Excimer laser), the threshold value is about 50 mJ per $cm^2$ per pulse, and the saturation value is about 250 mJ per $cm^2$ per pulse. Suitable energy densities at the corneal surface are 50 mJ per $cm^2$ to one J per $cm^2$ per pulse for a wavelength of 193 nanometers.

The threshold value can vary very rapidly with wavelength, and at 157 nanometers, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nanometers (under which conditions the saturation value is 250 mJ per $cm^2$ per pulse), it is preferable to provide to the cornea pulses of an energy density of about 90 to about 220 mJ per pulse. Typically, a single pulse will erode a depth in the range 0.1 to 1 micrometer of collagen from the cornea.

The pulse repetition rate for the laser may be chosen to meet the needs of each particular application. Normally, the rate will be between 1 and 500 pulses per second, preferably between 1 and 100 pulses per second. When it is desired to vary the beam size, the laser pulses may be stopped while the aperture or other beam shaping mechanism is changed. Alternatively, the beam size may be varied while the pulses continue. If a measurement device is used to monitor the erosion progress and control the laser system automatically, the beam size may be varied continuously at a controlled rate without interrupting the pulses.

In FIG. 2, one embodiment of a light restricting means 14A for use in the system of FIG. 1 is shown. In this embodiment, an adjustable iris 15 is employed to vary the exposure area over time. The leaves 15A of the adjustable iris can be programmed to slowly open (or conversely, slowly close), such that central region of the cornea receives a greater cumulative dose of ablative radiation than the peripheral regions. By controlling the number of pulses emitted for each setting of the aperture and controlling the aperture size, the actual profile of the eroded surface of the cornea can be very closely controlled. FIGS. 3A –3D are schematic illustrations of how the beamshaping element of FIG. 2 can operate to decrease the curvature of the cornea by selectively ablating tissue.

In FIG. 3A, the intact surface layers of the cornea 42 are shown comprising the epithelium 60, Bowman's membrane 62, and the upper portion of the stroma 64. In FIG. 3B, a large aperture is employed to ablate all (or a substantial portion) of the epithelial layer 60 of the cornea 42 in a region of the optical zone so as to expose the surface of Bowman's membrane 60. A first ablation region of wide, cross-sectional area is then created in Bowman's membrane 60 as shown in FIG. 3C. A narrower region of further ablation as shown in FIG. 3D is then created by employing a smaller aperture. The net effect is to create a flattened curvature. It should be clear that the actual procedure would be carried out with substantially greater number of steps in order to achieve a smooth curve and minimize the step-affects. In some applications, it is preferable to use an "opening iris" rather than a "closing iris," as illustrated in FIGS. 3B–3D; in this approach, the aperture is first set with a small opening and then progressively opened larger. The net result is the same: a general flattening of the corneal surface. Upon completion of the laser surgery, the epithelium regrows with a uniform thickness and produces a new corneal curvature determined by the reprofiling of the Bowman's membrane tissue. In certain applications, it may be preferable to employ a wider optical zone and also ablate with penetration into the stroma 64.

Figure 4A:
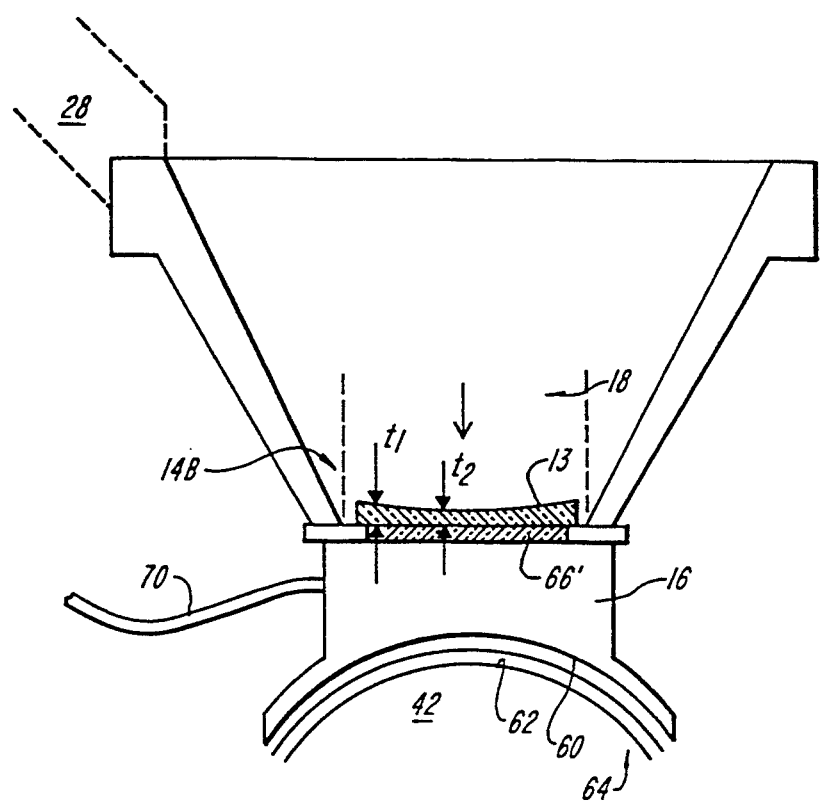
FIGS. 4A and 4B illustrate diagrammatically an alternative light restricting mechanism employing an erodable mask for use in the system of FIG. 1 to correct myopia.
Figure 4B:
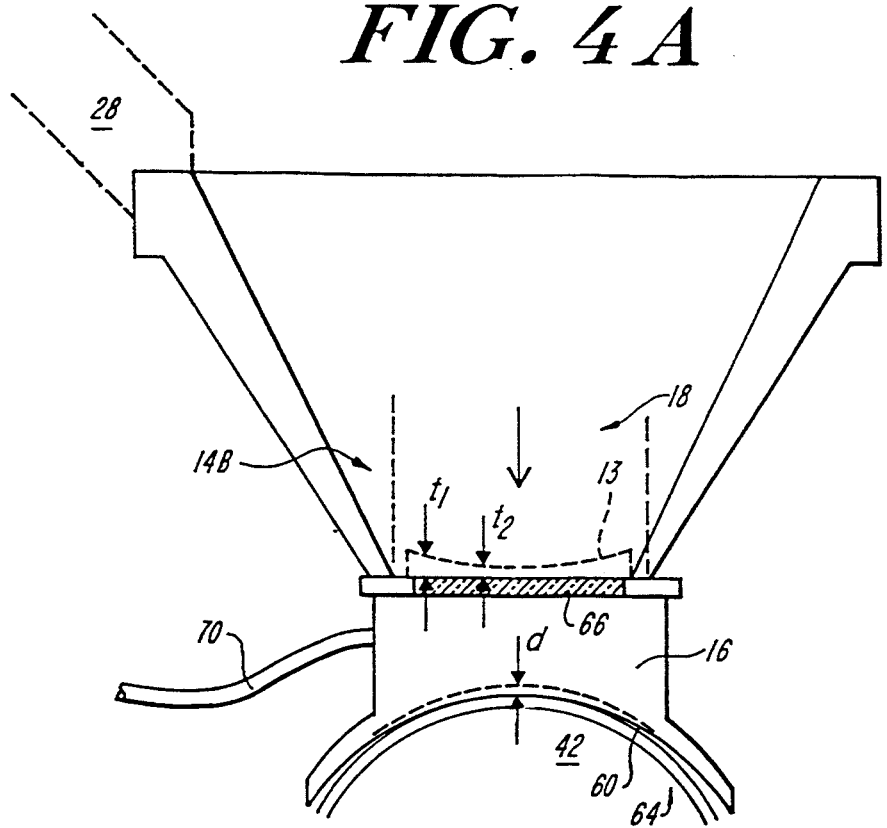

In FIGS. 4A and 4B, an alternative embodiment of the beamshaping means 14B of FIG. 1 is shown in more detail. As illustrated, the beamshaping means 14B includes a mask element 13 incorporated into an eye cup or similar eye secure means 16. As illustrated, the eye cup 16 provides a support structure having substantially rigid walls and a horizontal surface upon which the mask is disposed. In the illustrated embodiment, the masking means 13 is an erodable mask, and it is disposed upon a transparent stage 66.

The entire structure can be placed upon the sclera of an eye, leaving the corneal surface unobstructed. A flexible tube 70 can either supply vacuum suction to the cup so as to clamp it to the eye or provide a flow of gas for removal of ablation residue. For further details on the structure and composition of erodable masks, see U.S. Pat. Nos. 4,856.513 and 4,994,058, herein incorporated by reference.

FIG. 4B illustrates the principle involved in eroding a surface to effect reprofiling with a mask element. In FIGS. 4A and 4B, the surface layers of the cornea 42 are again shown, including the epithelium 60, Bowman's membrane 62, and the upper portion of the stroma 64. The mask 13 is uniformly irradiated with a beam of radiation 18 obtained from the laser source shown in FIG. 1.

During irradiation, the mask 13 is gradually ablated, and an increasing area of the cornea becomes exposed to laser ablation. At the moment when the mask 13 has been wholly ablated, the surface of the cornea has been eroded as indicated, to the extent necessary to complete the reprofiling over the area of the lens. As shown in FIGS. 4A–4B, the maximum thickness $t_1$ of the mask exceeds the minimum thickness $t_2$ by an amount equal to the maximum depth (d) of the corneal erosion desired. By controlling the shape, thickness and/or composition of the mask 68, photoablation of the cornea can be precisely confined to either Bowman's membrane 62 or the upper portions of the stroma 64. FIGS. 4A and 4B again illustrate a laser surgical techniques technique for correction of myopia. Similar lenses of appropriate shape can of course, be employed to remedy other forms of refractive errors, such as hyperopia, astigmatism and abnormal growths within the epithelium or the cornea.

Figure 5:
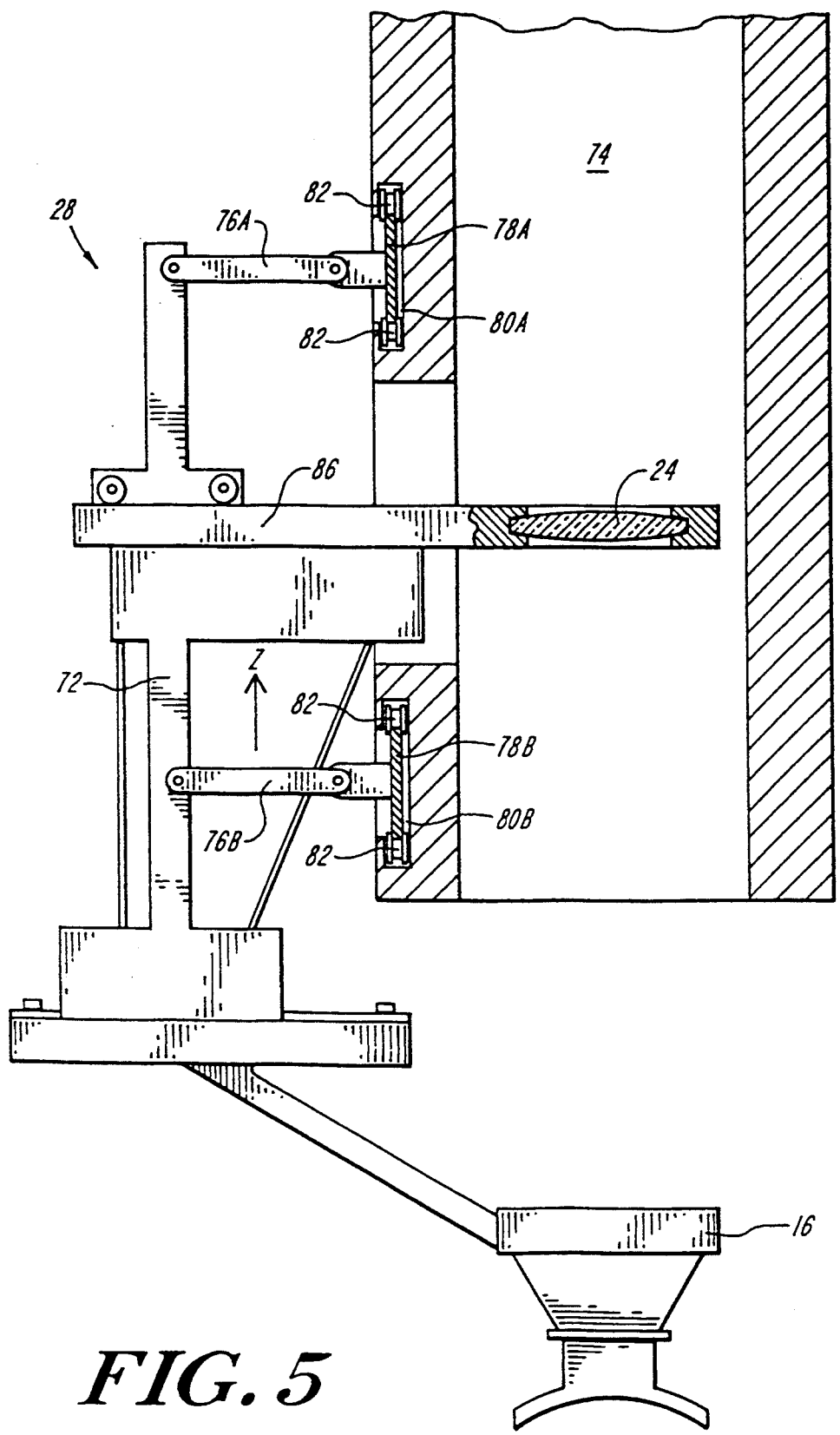
FIG. 5 is a more detailed schematic front view of a tracking system for laser ophthalmic surgery, in accordance with the invention illustrating tracking motion in the Z direction.
Figure 6:
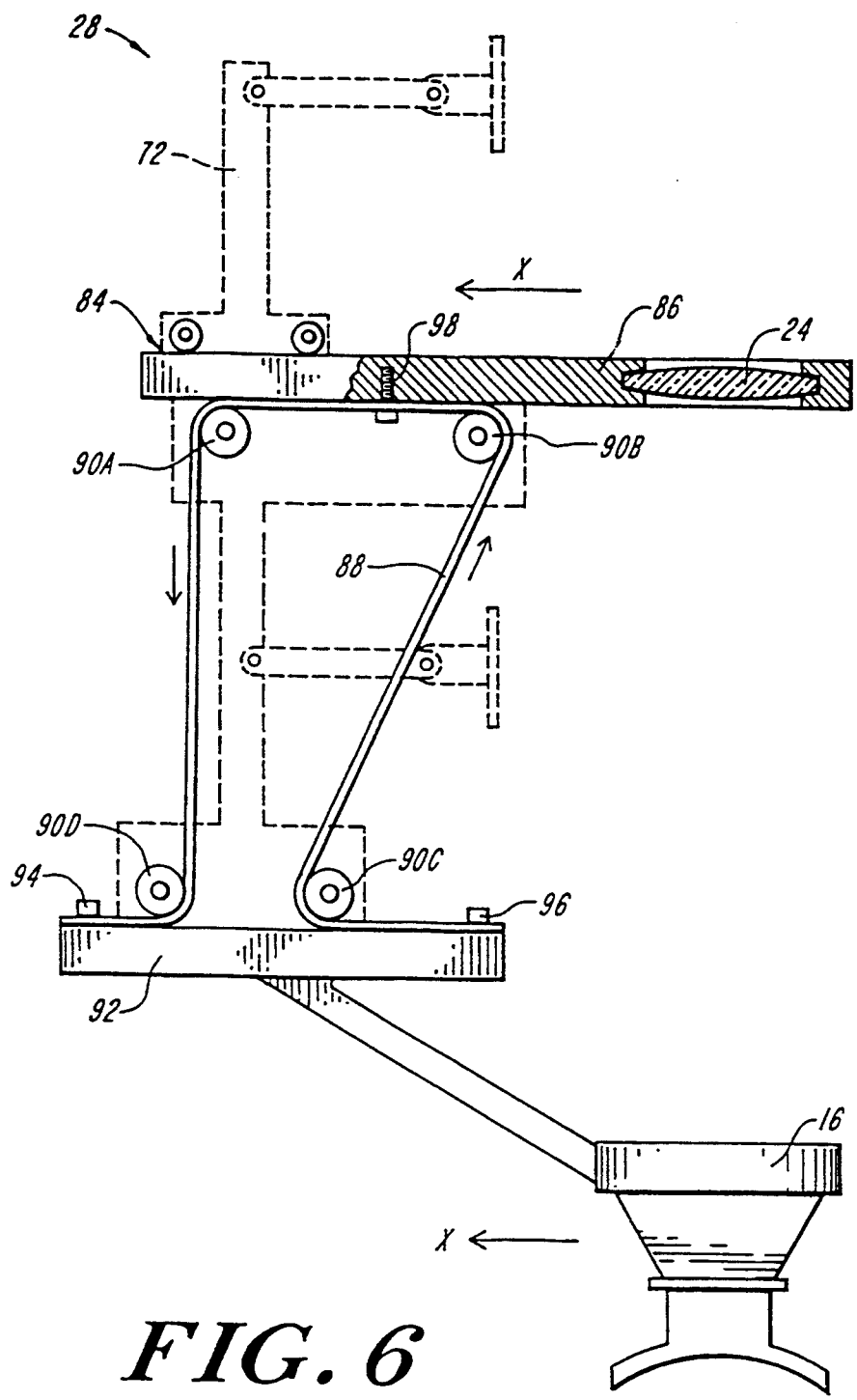
FIG. 6 is a similar schematic front view of the system of FIG. 5 illustrating tracking motion in the X direction.
Figure 7:
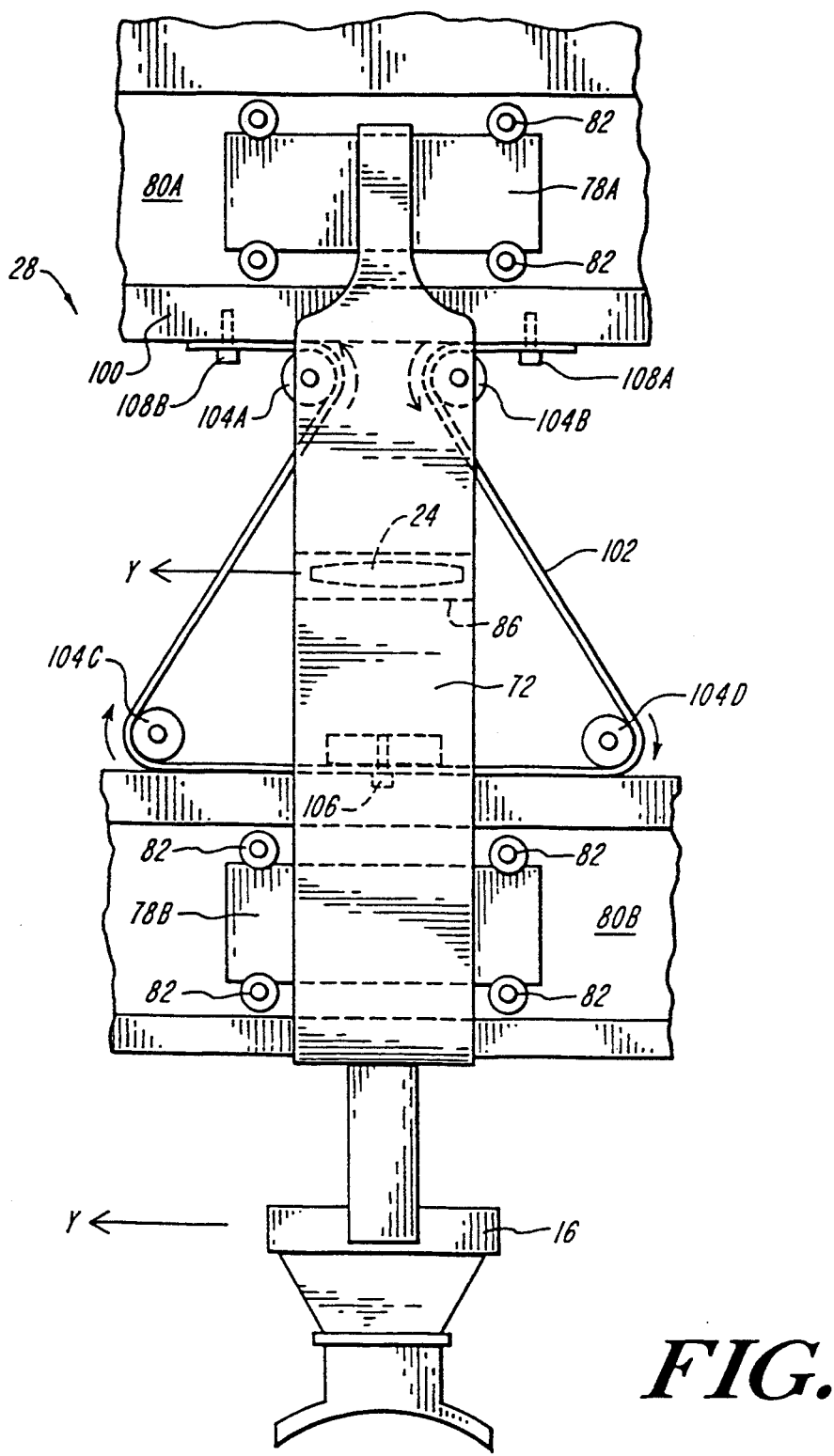
FIG. 7 is a side view of the system of FIGS. 5 and 6 illustrating tracking in the Y direction.

In FIGS. 5–7, a mechanical linkage assembly 28 for coupling a target securing element 16 and a floating optical element 24 is shown in more detail. Typically, the target securing element 16 will inherently restrain angular or rotational movements of the target vis-a-vis the laser; this is particularly true with respect to cornea eyecup-type devices which essentially prevent rotational movements of the eye. Thus, the movements, for which compensation must be provided, are constrained to translational motions in the X,Y or Z directions (or combinations thereof).

With reference first to FIG. 5, linkage assembly 28 can include a first linkage rod 72 or similar linkage means for tracking motion in the Z-direction. The linkage rod 72 serves to connect the eye cup 16 (or other target reference member) with a horizontal runner 86 which carries the floating optical element 24. The linkage rod 72 is joined to the laser beam delivery tube 74 by one or more pivot arms, e.g., arms 76A and 76B, as shown in FIG. 5. In the illustrated embodiment, the linkage 72 is connected indirectly to the laser delivery assembly 74 by runners 78A and 78B which permit the assembly 28 to move in lo channels 80A and 80B along the Y-axis (with the assistance of bearings 82.) Nonetheless, the pivot arms 76A and 76B permit movement of linkage rod 72 up and down along the Z-axis, such that movement of eyecup 16 results in a commensuration movement of floating lens 24.

In FIG. 6, linkage rod 72 is shown in phantom with further elements of the linkage assembly 28 superimposed on it in order to illustrate the tracking motion of the assembly with respect to movement of the eyecup 16 along the X-axis. Linkage rod 72 includes a channel 84 (or similar guide) which permits runner 86 to move the left or right. Belt 88 and pulleys 90A, 90B, 90C and 90D cooperate to provide X-directional tracking motion. As illustrated, belt 88 is fixed to flange 92 at both of its ends by pins 94 and 96. Whenever eyecup 16 moves in the X-direction, belt 88 is pulled through the pulleys 90A–90D. Because belt 88 is also fixed to runner 86 by pin 98, the movement of belt 88 around the pulleys, also causes movement of the runner 86 which carries with it floating lens 24.

A similar belt mechanism tracks movements in the Y-direction. FIG. 7 is a side view of the linkage assembly 28 illustrated in FIGS. 5 and 6, showing Y-direction motion. In FIG. 7, belt 102 is fixed at its two ends to guide rail 100 by pins 108A and 108B. When eyecup 16 moves in the Y-direction, belt 102 is pulled through pulleys 104A, 104B, 104C and 104D, because belt 102 is also attached to rod 72, e.g., by pin 106. Thus, floating lens 24 (which is linked to rod 72 by runner 86) moves with the eyecup 16 because belt 102 pulls the assembly along the channels 80A and 80B in the beam delivery housing 74.

Figure 8:
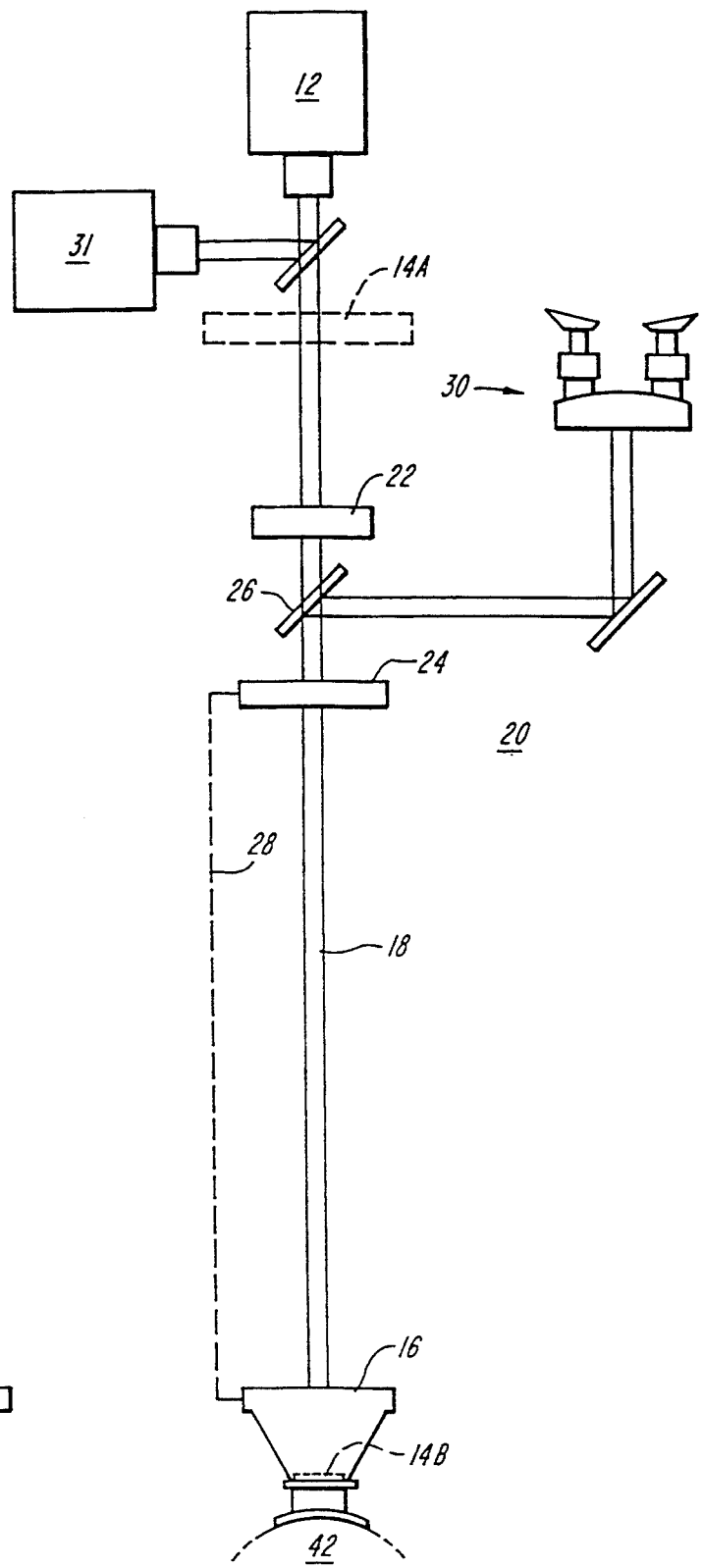
FIG. 8 is a diagrammatic illustration of a binocular, surgical microscope for use in connection with tracking systems according to the invention.

As shown in FIG. 8, the tracking system 20 of the present invention optionally can also be used in conjunction with a surgical microscope 30 or the like for viewing an eye or other target region during the laser treatment procedure. As shown in FIG. 8, a beam splitting element 26 (e.g., a dichotic mirror or the like) is disposed between fixed optical element 22 and floating optical element 24, such that the target surface can be visualized by the clinician during the procedure. (The microscope 30 can also include appropriate UV filter elements to ensure that the view is not exposed to reflected UV radiation.) A visible light source 31, also aligned with the optical axis, can be used to illuminate the target region and further enhance viewing.

What is claimed is:

1. A system for tracking target tissue movements during laser surgery comprising:
   a laser source for emitting laser radiation;
   target securing means for securing target tissue region during surgery; and
   optical means for projecting the laser radiation onto said target region, the optical means further comprising:
   at least one fixed optical element which is fixed in position during surgery; and
   a floating optical element which is mechanically coupled to the target securing means for movement therewith, whereby the fixed optical element and the floating element from an imaging system in which movements of target tissue region are tracked by the floating optical element, such that the laser radiation remains imaged upon the target region.

2. The system of claim 1 wherein the target securing means further comprises an eye cup adapted to be mounted upon the sclera of an eye.

3. The system of claim 1 wherein the target securing means further comprises a light restricting means for varying an exposure area within the target region over time.

4. The system of claim 3 wherein the light restricting means is a masking means.

5. The system of claim 4 wherein the masking means further comprises an erodable mask.

6. The system of claim 1 wherein the optical means further comprises a first fixed lens element and a second floating lens element which cooperate to define an image plane at the surface of the target region.

7. The system of claim 1 wherein the floating optical element further comprises a translational stage which provides for tracking of movements of the target securing means by the floating optical element in at least two orthogonal directions.

8. The system of claim 7 wherein the translational stage provides for tracking in three orthogonal directions.

9. The system of claim 1 wherein the optical means further comprises a beamsplitter disposed between the fixed and floating optical elements to permit viewing of the target region during surgical procedures.

10. The system of claim 9 wherein the system further comprises a surgical microscope optically coupled to the beam splitter for viewing the target region.

11. The system of claim 10 wherein the system further comprises a source of visible light optically coupled to the beam splitter for illuminating the target region.

* * * * *